United States Patent [19]

Mardin et al.

[11] Patent Number: 4,540,707

[45] Date of Patent: Sep. 10, 1985

[54] NAFAZATROM AS A LIPOXYGENASE INHIBITOR

[75] Inventors: Mithat Mardin, Wuppertal, Fed. Rep. of Germany; Wolf-Dieter Busse, West Haven, Conn.; Friedrich Hoffmeister, Wuppertal, Fed. Rep. of Germany; Friedel Seuter, Wuppertal, Fed. Rep. of Germany; Elisabeth Perzborn, Wuppertal, Fed. Rep. of Germany; Klaus Schlossmann, Wuppertal, Fed. Rep. of Germany; Dieter Mayer, Werne, Fed. Rep. of Germany; Volker Fiedler, Wuppertal, Fed. Rep. of Germany

[73] Assignee: Bayer Aktiengesellschaft, Leverkusen, Fed. Rep. of Germany

[21] Appl. No.: 486,175

[22] Filed: Apr. 18, 1983

[30] Foreign Application Priority Data

Jan. 28, 1983 [DE] Fed. Rep. of Germany ....... 3302811
Mar. 12, 1983 [DE] Fed. Rep. of Germany ....... 3308880

[51] Int. Cl.$^3$ ............................................ A61K 31/415
[52] U.S. Cl. ..................................... 514/404; 514/821
[58] Field of Search ...................................... 424/273 P

[56] References Cited

U.S. PATENT DOCUMENTS 4,053,621 10/1977 Möller et al. ...................... 424/245
4,372,887 2/1983 Wu et al. ............................. 424/274

OTHER PUBLICATIONS

R. Lucchesi et al., Overview, August M. Watanabe, 1984, Clinical Pharmacology of Antiarrhythmic Therapy, pp. 73–76.

*Primary Examiner*—Frederick E. Waddell
*Attorney, Agent, or Firm*—Sprung Horn Kramer & Woods

[57] ABSTRACT

A method of inhibiting lipoxygenase in a patient, for the prophylaxis and/or treatment of ischaemias and disorders in cardiac rhythm and of rheumatic, allergic and asthmatic diseases, oedemas, pulmonary embolisms, pulmonary hypertension, oxygen intoxications and ulcerations which comprises administering to such patient an effective amount of nafazatrom.

1 Claim, No Drawings

NAFAZATROM AS A LIPOXYGENASE INHIBITOR

The present invention relates to the use of 3-methyl-1-[2-(2-naphthyloxy)-ethyl]-2-pyrazolin-5-one ("nafazatrom") as a lipoxygenase inhibitor for the prophylaxis and treatment of ischaemias, in particular of cardiac infarctions following myocardial ischaemias, and disorders in cardiac rhythm, rheumatic, allergic and asthmatic diseases, pulmonary embolisms and oedemas (in particular pulmonary oedemas), pulmonary hypertension, oxygen intoxication and ulcerations. The invention also relates to lipoxygenase-inhibiting, bronchodilatory, antiarrhythmic, antiischaemic, antirheumatic, antiallergic, antiasthmatic, antioedemic, antihypertensive and gastroprotective medicaments which are characterized in that they contain a therapeutically active amount of nafazatrom.

It is known that nafazatrom has a powerful antithrombotic action (DE-AS [German Published Specification] No. 2,427,272 and U.S. Pat. No. 4,053,621), but can also be used for reducing metastases formation and neoplastic growth in mammals (European patent application No. 0,062,319).

As an antithrombotic agent, nafazatrom was effective arterially and venously (v.jugularis, a.carotis and a.femoralis in animal experiments, for example on rats, guinea pigs and rabbits (Seuter et al., Arzneim. Forsch. 29, 54, 1979), and was also effective in the coronary arteries of dogs.

Several investigations with nafazatrom have shown that the substance can act as a stimulator of endogenous prostacyclin ($PGI_2$) from the vascular endothelium (Vermylen et al., Lancet I, 528, 1979, Chamone et al., Haemostasis 10, 297, 1981 and McIntyre and Salzman, Thrombosis and Haemostasis, 46, Abstract No. 45, 1981). Wong and McGiff (J. Pharmacol. Exp. Ther. 223, 757–760, 1982) have also shown that nafazatrom blocks 15-hydroxyprostaglandin dehydrogenase, the $PGI_2$-degrading enzyme.

As a surprising new action quality, it has now been found that nafazatrom inhibits lipoxygenase activity, which is responsible for biosynthesis of the chemotactically active leukotriene $B_4$ and the spasmogenically active leukotrienes $C_4$ and $D_4$.

Known lipoxygenase inhibitors, such as nordihydroguaiaretic acid, 3-amino-1-(3-trifluoromethylphenyl)-pyrazoline (BW 755 C), phenidone and 5,8,11,14-eicosatetrainoic acid, have the disadvantage that they are either at the same time active as cyclooxygenase inhibitors or active only in very high concentrations. Inhibition of the enzyme cyclooxygenase from the metabolism of arachidonic acids leads to a global inhibition of prostaglandin synthesis and to a stimulation of the lipoxygenase path, which can cause gastrotoxicity, inflammation-promoting and asthmatic actions and an increased tendency towards thromboses as a result of inhibition of prostacyclin synthesis.

No such inhibition of cyclooxygenase occurs on administration of nafazatrom. In contrast, nafazatrom exhibits a marked antiasthmatic, inflammation-inhibiting and gastro-protective action.

Surprisingly, nafazatrom selectively inhibits the 5-lipoxygenase responsible for biosynthesis of the leukotrienes $B_4$, $C_4$ and $D_4$, while the 15-lipoxygenase responsible for biosynthesis of the endogenous lipoxygenase inhibitor 15-hydroxyeicosatetraenoic acid (15-HETE) is not inhibited or is even stimulated at concentrations of >10 µg/ml. Likewise, the 12-lipoxygenase activity is not inhibited by these concentrations of nafazatrom. Furthermore, nafazatrom specifically stimulates synthesis of prostacyclin ($PGI_2$).

Inhibition or stimulation of the individual enzymes of arachidonic acid metabolism can also lead indirectly to non-specific $PGI_2$ stimulation. Thus, nafazatrom acts as a reducing cofactor of the hydroperoxidase portion of cyclooxygenase and accelerates the conversion of arachidonic acid into $PGH_2$ (T. E. Eling et al., Prostaglandins and Cancer: First International Conference, 783–787, 982, Alan R. Liss, Inc., New York). In the endothelial cells, $PGH_2$ serves as a starting substance for synthesis of $PGI_2$, and also for the synthesis of $PGE_2$, $PGF_2\alpha$, $PGD_2$ and $TXA_2$. In contrast to $PGI_2$, however, the latter compounds have a vasoconstricting action, intensified platelet aggregation ($PGE_2$, $PGF_2\alpha$) or induce aggregation ($TXA_2$). Surprisingly, however, only $PGI_2$ synthesis is stimulated in the presence of nafazatrom, while the synthesis of the prostaglandins having a vasocontricting action and of $TXA_2$ is not influenced (see Example 2).

As investigations on rabbit hearts perfused by the method of Langendorff have shown (see Example 3), nafazatrom also displays vasodilating effects locally, these being particularly of therapeutic use in ischaemic tissue (for example heart, brain and periphery). In contrast to indomethacin, which has an overall inhibiting action on the synthesis of prostaglandins from arachidonic acid, nafazatrom intervenes much more specifically in the metabolism of the enzymes decisive for the formation of $PGI_2$, thromboxan and the leukotrienes, so that not only is the harmful, vasoconstricting and arrhythmia-increasing influence of thromboxan and the leukotrienes reduced, but also the vasodilating influence of the prostacyclin is increased by stimulation of its formation. The fact that nafazatrom very clearly reduces or excludes the harmful effect of a sudden influx of oxygen following a hypoxic or anoxic period is shown in particular by the results in the reoxygenation phase. Damage by reoxygenation can occur after bypass operations. Nafazatrom is therefore suitable for preventing oxygen damage in such operations.

Surprisingly, it has also been found that nafazatrom reduces the stickiness of leucocytes, that is to say it increases their rate of migration. The leucocyte mobility was tested on the following in vivo model: in venules having a diameter of 30–40 µm, the number of leucocytes per unit time flowing past a fixed point, specified at the start of the experiment, of the vessel is counted. If the stickiness of the leucocytes is now increased, the leucocytes stick and the number of leucocytes passing the point decreases. Correspondingly, the number of leucocytes passing per unit time is increased if the leucocyte stickiness decreases (see example).

The reduction in the stickiness of leucocytes by nafazatrom likewise contributes to a decrease in ischaemic areas, since, after treatment with nafazatrom, the leucocytes pass through the microcirculatory area of these regions without causing restricted supply to corresponding tissues as a result of total or temporary closure of small vessels or capillaries.

Nafazatrom can moreover be used for the therapy of pulmonary hypertension, pulmonary embolisms and pulmonary oedemas. The bronchodilating properties of the active compounds can be demonstrated, for example, on isolated lungs of guinea pigs. In this organ, nafazatrom inhibits (by the method of F. P. Luduena et al., Arch. Int. Pharmacodyn. 111, 392, 1957) methacholine-induced bronchoconstriction (see Example 5).

Reduction in cardiac infarctions following myocardial ischaemias and a positive influence on disorders in cardiac rhythm have been found as further surprising action qualities of nafazatrom (see Example 6). These intended uses, according to the invention, of nafazatrom are also not suggested by its abovementioned indications known from the prior art.

Substances for the therapy of disorders in cardiac rhythm are classified according to their electrophysiological actions.

Since the classification of Vaughan Williams (Pharmac. Ther. B 1, 115, 1975), the following classes are differentiated:

(I) Membrane-stabilizing antiarrhythmic agents of
   (a) the quinidine type, for example procaine and ajmaline, and
   (b) the lidocaine type, for example lidocaine and diphenylhydantoin
(II) Beta-receptor blockers, such as, for example, propanolol and many others.
(III) Calcium antagonists, such as, for example, verapamil, nifedipine and many others.
(IV) Substances with an increase in the duration of action potential, such as, for example, amiodarone.

The active compound nafazatrom cannot be subclassified under the above groups either on the basis of its chemical structure or on its haemodynamic actions known hitherto. For this reason, it could not be predicted that nafazotrom displays antiarrhythmic effects. On the basis of the antithrombotic action, it was just as unlikely that nafazatrom, as has been found, greatly restricts the spread of myocardial ischaemia after vascular occlusion—and in particular independently of the nature of occlusion of the coronary vessel—and thus reduces the size of infarction and moreover leads to more rapid healing. As animal experiments have demonstrated, nafazatrom reduces the ischaemia-induced rise in the ST zone as an indication of infarction; moreover, it has been found that the R-wave in the ECG of the peripheral extremities increases less sharply and re-forms more rapidly, and that ST intervals are changed less than in the controls, which leads to the conclusion that repolarization of the cardiac muscle cells is improved.

As has been described in U.S. Pat. No. 4,053,621, the nafazatrom (represented by formula I, which follows) to be used according to the invention can be prepared by various synthesis routes, as illustrated below. In process A, 2-(2-naphthyloxy)-ethylhydrazine is reacted with an acetoacetic acid derivative; in process B, 3-methylpyrazolin-5-one is reacted with a 2-2-naphthyloxy)-ethyl derivative; in process C, 2-(2-naphthyloxy)-ethylhydrazine is reacted with a tetrolic acid derivative.

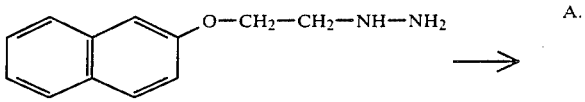

All the inert organic solvents, if desired diluted with water, for example hydrocarbons, such as benzene and toluene, halogenohydrocarbons, such as methylene chloride, alcohols, such as methanol and ethanol, and organic bases, such as pyridine and picoline, are suitable as the reaction medium.

Basic or acid condensing agents can be used for the above processes for the preparation of nafazatrom, and the reaction temperature can be varied between 10° C. and 200° C. The compound can be purified in a simple manner by means of customary methods, by recrystallization from a suitable solvent.

In addition to nafazatrom, the medicaments according to the present invention also contain pharmaceutically acceptable diluents or excipients. By these, there are to be understood non-toxic substances which, after being mixed with the active compound, render the active compound in a form suitable for administration. The term preferably excludes water and organic solvents of low molecular weight usually employed in chemical synthesis, apart from when other pharmaceutically required constituents are present, such as salts in the correct amounts to prepare an isotonic formulation, buffers, surface-active agents, colorants and flavoring agents and preservatives. The following substances are examples of suitable solid and liquid diluents and excipients: water-containing buffers which can be rendered isotonic by the addition of glucose or salts; non-toxic organic solvents, such as paraffins, vegetable oils, alcohols and glycols; ground natural rock materials (for example kaolins, aluminum oxides, talc or chalk); synthetic rock powders (for example highly disperse silicic acid or silicates); and sugars.

The medicaments according to the invention as a rule contain 0.5–95% by weight, preferably 1–90% % by weight and particularly preferably 5–50% by weight, of nafazatrom.

Oral administration can be effected using solid and liquid dosage forms, such as powders, tablets, dragees, capsules, granules, suspensions, solutions and the like. If desired, the dosage units can be microencapsulated for oral administration in order to delay release or to slow it down over a longer period, such as, for example, by coating or embedding particulate material in polymers, wax or the like.

Parenteral administration can be effected using liquid dosage forms, such as sterile solutions and suspensions, which are intended for subcutaneous, intramuscular or intravenous injection. These dosage forms are prepared by suspending or dissolving a measured amount of the active compound in a non-toxic liquid extender suitable for injection, such as an aqueous or oil medium, and sterilizing the suspension or solution. Stabilizers, preservatives and emulsifiers can likewise be added.

In general, the daily dose of active compound for humans, based on the body weight, is 0.01 to 50 mg/kg, preferably 0.1 to 10 mg/kg, for parenteral administration and 0.1 to 500 mg/kg, preferably 0.5 to 100 mg/kg and particularly preferably 1 to 50 mg/kg, for oral administration.

The dosage unit (tablet, capsule and the like as a rule contains 1–100 mg, preferably 5–50 mg and particularly preferably 10–30 mg, of nafazatrom.

EXAMPLE 1

Lipoxygenase-Inhibiting Action

The human PMN Leucocytes (95%) used in the present example were obtained from heparinized complete blood by dextran sedimentation and subsequent density gradient separation (Ficoll-Paque) (compare A. Boyuim, Scand. J. Immunol., 5, Suppl. 5, 9, 1976).

$2 \times 10^7$ cells/ml were suspended in Dulbecco phosphate buffer containing $Ca^{2+}$ and were incubated with radioactively labelled arachidonic acid and the calcium inonophor A 23187 in the presence or absence of lipoxygenase inhibitor. After 15 minutes, the labelled lipoxygenase products were extracted from the acidified incubation medium and were separated by thin layer chromatography using a mobile phase mixture suitable for the leukotrienes (5-HETE-LTB$_4$) (compare B. Jakschik et al., Biochem. Biophys. Res. Commun., 102, 624, 1981).

The distribution of the the activity amongst the various metabolites was measured by a thin layer scanner. It is a measure of the lipoxygenase-inhibiting action of a test substance at a certain concentration.

The lipoxygenase metabolites were also additionally determined independently by means of high pressure liquid chromatography. This method enables the endogenous arachidonic acid metabolism to be studied with the aid of UV detection of the leukiotrienes. In this method, the cells were treated as described above, with the exception that no radioactively labelled arachidonic acid was added exogenously. The high pressure liquid chromatography was carried out on Lichrosorb RP-18 (5 μm) columns. The mobile phase was methanol/water/glacial acetic acid 69/31/0.01. The flow rate was 1 ml/minute. Leukotriene B$_4$ was determined at 232 nm, in each case by means of UV absorption.

Nafazatrom inhibits LTB$_4$ biosynthesis in the concentration range of 1–10 μg/ml as a function of the concentration, as shown by the following Table 1:

TABLE 1

| Lipoxygenase inhibition by nafazatrom: inhibition of Leukotriene B$_4$ biosynthesis in human PMN Leucocytes | |
|---|---|
| Nafazatrom [ug/ml] | Inhibition in % in comparison with the control |
| 10 | 100 |
| 5 | 90 |
| 3 | 75 |
| 1 | 30 |

EXAMPLE 2

Specific Stimulation of Prostacyclin Synthesis

The specific PGI$_2$-stimulating action of nafazatrom was shown in vitro in a mixture of microsomes from the seminal vesicles of sheep (RSVM) and the aortas of cattle (BAM) (compare F. Cottee et al., Protaglandins, 14, 413, 1977). $^3$H-arachidonic acid was incubated with a mixture of RSVM and BAM in the presence of $3 \cdot 10^{-5}$ g/ml of nafazatrom at 25° C. for 10 minutes. The reaction was stopped by acidification to pH 3.5. The fatty acid metabolites were extracted with ethyl acetate. The ethyl acetate was evaporated off under N$_2$, the residue was taken up in CH$_3$OH/CHCl$_3$ (1:1) and the mixture was discharged on thin layer chromatography plastic sheets. Separation was effected with a mobile phase mixture of ethyl acetate/glacial acetic acid/isooctane/H$_2$O (110:20:50:10; organic phase) (P. Needleman et al., The Journal of Clinical Investigation 1978, 61, 839–849). The distribution of the radioactivity was measured by means of a radio scanner.

The table which follows shows the influence of nafazatrom ($3 \cdot 10^{-5}$ g/ml) on the synthesis of various prostaglandins in RSVM in comparison with the control experiment without nafazatrom.

TABLE 2

| Prostaglandin | Increase in concentration (in %) in comparison with the control |
|---|---|
| 6-Keto-PGF$_1\alpha$ | 300–400 |
| PGD$_2$ | 0 |
| PGE$_2$ | 0 |
| PGF$_2\alpha$ | 0 |

EXAMPLE 3

Action of Nafazatrom on Rabbit Hearts Perfused by the Method of Langendorff

The heart was removed from the rabbits (up to about 2 kg) under Nembutal anaesthesia and cannulas were attached at the aorta and at the a.pulmonalis. To measure the isovolumetric contractions, a silicon rubber balloon filled with liquid was inserted into the left ventricle via the left auricle. The balloon was connected to a liquid sensor (Statham P 23 Db) via a liquid bridge. The perfusion pressure was recorded with a pressure sensor, which was connected to the perfusion system via T-piece before the aorta cannula of the heart. The contraction force and perfusion pressure were recorded with a Gould 2600 S high-speed recorder. The hearts were stimulated electrically at a frequency of 180/minute and a stimulation duration of 5 mseconds.

Perfusion of the hearts was effected with Krebs-Henseleit solution (KH solution), which was gassed with carbogen (95% of $O_2$, 5% of $CO_2$) or with a gas mixture of 2% of $O_2$, 5.6% of $CO_2$ and the remainder $N_2$. The perfusion volume was 20 ml/minute and was adjusted by a roller pump (Desaga, 132100). The nafazatrom and the platelet suspensions (obtained from the same rabbit from which the heart is removed) were added with the aid of infusion pumps (roller pumps, Braun-Melsungen), the solution or suspension being infused at a flow rate of 0.2 or 0.1 ml/minute from an infusion syringe via a Taigon tube and a fine cannula into the inlet tube shortly before the heart. The final concentration of the platelets was $1 \times 10^7$/ml of KH solution. The solution flowing out of the heart (cannula in the a.pulmonalis) was collected periodically, under ice-cooling. To measure the concentrations of thromboxan as TXB$_2$ and of prostacyclin as 6-keto-PGF$_1\alpha$, determination of which was effected with the aid of radioimmunoassay, aliquot parts by volume were freeze-dried and taken up in one tenth of the original volume of water.

The perfusion pressure values found in the experiments on administration of nafazatrom can be seen in comparison with those of the control in Table 3 which follows:

TABLE 3

| | Perfusion pressure in % of the blank value | | | | |
|---|---|---|---|---|---|
| | 1st phase | 2nd phase | 3rd phase | 4th phase | 5th phase |
| Control experiment | 100 | 155 | — | 83 | 214 |
| Addition of nafazatrom | 100 | 139 | 80 | 63 | 75 |

1st phase — preliminary phase; gassing with carbogen
2nd phase — normoxia; gassing with carbogen; addition of $1.10^7$ platelets/ml; duration: 5 minutes
3rd phase — as 2nd phase; addition of $1.10^{-5}$ g/ml of nafazatrom; duration: 5 minutes
4th phase — as 3rd phase, but gassing with only 2% of $O_2$ (hypoxia); duration: 10 minutes
5th phase — as 3rd phase (reoxygenation).

The results show that when platelets are added to the perfusion solution, there is a significant rise in the perfusion pressure in comparison with the preliminary phase. If perfusion is effected with a solution of low oxygen content (2% of $O_2$) in the subsequent phase, the perfusion pressure and the contraction force drop markedly. On subsequent reoxygenation (gassing with carbogen), the contraction force recovers to approximately the same values as before the period of hypoxia; however, the perfusion pressure rises beyond the pressure level in the first carbogen phase.

It is surprising that nafazatrom significantly inhibits the rise in perfusion pressure caused by addition of platelets to the perfusion solution in the first and second carbogen phase. This effect is particularly pronounced in the reoxygenation phase following the hypoxia phase.

EXAMPLE 4

Leucocyte Stickiness

The number of leucocytes which pass a certain section of a vessel serves as a simple model for measuring the stickiness of leucocytes (Bray, M. A. et al., Prostaglandins 22, 213 (1981)). The number of leucocytes counted will be greater, the lower the stickiness of the cells.

Nafazatrom was investigated in this model.

Male Syrian golden hamsters (80–100 g) were anaesthetized with Nembutal (i.p.; 60 mg/kg). After insertion of a PE 10 catheter into the a.femoralis, the animal was laid on a Duling dissecting platform (MVR 5, 423 (1973)) and the right cheek pouch was withdrawn by inserting a Q-Tip. It was carefully drawn into the envisaged part of the platform, stretched and fixed.

From the start of the dissection, 5 ml/minute of Superfusat flowed over the prepared cheek pouch. The temperature of the solution is 36° C. While treating the vessels with care, the upper layer tissue was separated longitudinally and folded back to the side. Under about 200-fold magnification, an area of about 1 cm$^2$ of connective tissue was carefully exposed. The animal was placed on the object stand of a microscope, together with the dissecting platform. A thermocouple was inserted into the left cheek pouch. The body temperature of the animal was thus monitored and kept at ±0.3° C. with the aid of an IR lamp (250 watt).

The leucocyte stickiness was measured at about 500-fold magnification. A venule (30–40 μm φ) was selected in the exposed area. The number of leucocytes per unit time (minutes) which migrate past a certain section of this vessel was counted.

Intraarterial administration of 1.0 mg/kg of nafazatrom led to an increase in the number of leucocytes of 60–100%. The duration of action was about 60 minutes.

EXAMPLE 5

Bronchodilating Action

The guinea pig lung was perfused with a physiological buffer solution (Tyrode's solution) containing 0.05 µg/ml of methacholine. The flow rate was reduced by the bronchoconstriction which took place, and the perfusion pressure was correspondingly increased. $10^{-4}$ g/ml of nafazatrom inhibited the rise in perfusion pressure, and hence bronchoconstriction, to the extent of 50%.

EXAMPLE 6

Ligation of the left coronary artery of the rat heart and the disorders in cardiac rhythm which thereby occur form a relatively simple model for investigating substances having antiarrhythmic actions and effects on the developing myocardial ischaemia (Clark et al., J. Pharmacol. Meth. 3, 357, 1980). The effects of nafazatrom on antiarrhythmic and antiischaemic properties in conscious rats was investigated in this model. Particular importance was placed on the severity and quantity of disorders in cardiac rhythm which occurred.

Male Wistar rats (250–350 g) were superficially anaesthetized with ether and investigated for rhythm disorders. Animals with rhythm abnormalities before the start of the experiment were excluded. In acute surgery, the animals were again anaesthetized with ether. In the lateral dorsal position, the thorax was opened somewhat to the left alongside the central line and the heart was exteriorized. Close below the left heart auricle, a silk ligature (3-0) was looped through the muscle of the left heart under the anterior coronary artery. Animals which developed rhythm disorders during this procedure were excluded. The left coronary artery was ligatured by the method described by Selye et al. (Angiology 11, 398, 1960), the heart was returned to the thorax and the wound was rapidly closed with thread. Since the thorax had not been opened for longer than about 45 seconds, artificial respiration of the animals was unnecessary. The operation mortality was between 25 and 40% within the first hours, and in particular myocardial haemorrhages, rhythm disorders with ventricular fibrillation, and massive cardiac infarctions occurred. In a sham-operated group, the same experimental conditions were investigated, with the exception that the coronary artery remained open. Shortly after the ligature had been made, early rhythm disorders were observed, which were accompanied in some cases (untreated) with ventricular fibrillations. In most cases, this ventricular fibrillation spontaneously turned into uniform sinus rhythm of heart contraction. The disorders in cardiac rhythm were evaluated by the plan described by Clark (see above). Ventricular tachycardia was defined as the result of more than 10 successive rhythm disorders with extrasystoles. Electrocardiographic changes included a rise in the ST segment, a drop in the Q waves and a rise in the QT interval. The total number of ectopic activity in each individual animal was determined by counting the ventricular extrasystoles, including tachycardia and fibrillations.

Three groups were investigated: group I received the diluent (1% strength aqueous Tylose suspension, that is to say methylhydroxyethyl-cellulose) twice daily perorally (0.5 ml/kg) for 10 days and by the same administration and in the same amount, after coronary ligature, for a further 20 days; group II was pretreated with the diluent for 10 days (0.5 ml/kg) and was treated with 30 or 100 mg/kg of nafazatrom (in each case suspended in 0.5 ml/kg of 1% strength Tylose suspension) twice daily perorally for 20 days, after coronary ligature (the first nafazatrom administration was effected immediately after the coronary ligature); group III received the above oral doses of nafazatrom in the course of 10 days before the ligature, and the diluent Tylose suspension for 10 days after the coronary occlusion had been effected. The sham-operated animals remained untreated. The peripheral ECG in the extremities was determined in lead II, and in particular, as a control before the start of treatment, shortly before and during coronary ligature, 10 minutes after coronary ligature had been effected, and—after renewed ether anaesthesia—between the 2nd and 4th hour after coronary occlusion. Each time, the animals were superficially anaesthetized again with ether when the ECG was recorded. At the end of the treatment period, a last ECG was recorded shortly before the animals were sacrificed. The readings were recorded on a Clevite-Gould multi-channel recorder.

At the end of the experiments, the heart was removed, after opening the thorax, from the sacrificed animal and, after being washed, was attached to a perfusion system. The hearts were flushed in retrograde fashion with a triphenyltetrazolium chloride solution (1.5% strength by weight aqueous solution; pH 7.4; 37° C.) under a pressure of 100–120 mm Hg for 30 minutes.

This solution stains tissues with NAD or NADP activity a luminous red color. The coloration depends on the enzymatic dehydrogenase activity. Since infarcted tissue has a reduced dehydrogenase enzyme activity, these deficient areas are stained only slightly greyish or not at all. After the heart had been removed from the perfusion apparatus, the heart auricles were removed and the ventricles were cut into transversal slices (5 mm) and fixed in 10% strength formalin solution for 24 hours. The slices of heart were then photographed with color film and the photographs were enlarged to give 18×24 cm colored photographs. The infarction size of each slice was then recorded from the photos by planimetry. The mean infarction size was expressed as a percentage of the weight of the heart and of the size of the heart.

The treatment with nafazatrom in groups II and III was compared with that of the control animals treated only with Tylose. The total mortality was 38% in the controls (Table 4) but only 22% or 12% in the animals after-treated with 30 or, respectively, 100 mg/kg of nafazatrom. No myocardial changes were found in the sham-operated animals. No significant differences were to be found between the two groups which received nafazatrom before or after coronary ligature. However, the infarctions were significantly smaller in both groups in comparison with the control animals treated only with Tylose. The nafazatrom pre-treatment reduced the infarction by 36 or 48% following administration of 30 or, respectively, 100 mg/kg of the substance. The treatment after coronary ligature reduced the infarction size by 28 or 39%.

The antiarrhythmic effects of the substance are recorded in Table 5. During the early phase of arrhythmias following coronary ligature (0–10 minutes) and in the late phase of rhythm disorders (2–4 hours after ligature), significantly fewer irregularities were observed in comparison with the control animals. With a pre-treatment of 100 mg/kg of nafazatrom, it was possible to prevent almost all the rhythm disorders observed in the animals treated only with Tylose. The substance thus reduced the number of extrasystoles and the occurrence and severity of ventricular arrhythmias, including the frequency of fibrillation, which were to be observed in the controls.

TABLE 4

Effect of nafazatrom on cardiac infarction size

| Group | Pre-treatment 10 days | After-treatment post-operation 20 days | Infarction size, % of total heart (number of animals in brackets) | Total mortality % |
|---|---|---|---|---|
| I | Tylose | Tylose | 43.7 (16) | 39 |
| II | Tylose | Nafazatrom (30 mg/kg, 2 × daily) | 31.5 (15) | 24 |
|  | Tylose | Nafazatrom (100 mg/kg, 2 × daily) | 26.7 (18) | 22 |
| III | Nafazatrom (30 mg/kg) | Tylose | 28.0 (12) | 22 |
|  | Nafazatrom (100 mg/kg) | Tylose | 22.7 (16) | 12 |

TABLE 5

Effects of nafazatrom on ventricular extrasystoles, the degree of ventricular tachycardia (VT) and of ventricular fibrillation (VF) in the early (0–10 minutes) and late phase (2–4 hours) of rhythm disorders following coronary ligature in rats (number of animals in brackets)

| Group | Pre-treatment 10 days | After-treatment post-operation 20 days | Extrasystoles % early | Extrasystoles % late | Duration of VT (seconds) early | Duration of VT (seconds) late | Duration of VF (seconds) early | Duration of VF (seconds) late |
|---|---|---|---|---|---|---|---|---|
| I | Tylose | Tylose | 100 (16) | 42 (8) | 65 (16) | 12 (8) | 60 (16) | 9 (8) |
| II | Tylose | Nafazatrom (30 mg/kg, 2 × daily) | 94 (15) | 6 (9) | 72 (15) | 4 (9) | 65 (15) | 0 (9) |
|  |  | Nafazatrom (100 mg/kg, 2 × daily) | 90 (18) | 0 (18) | 60 (18) | 0 (18) | 68 (18) | 0 (18) |
| III | Nafazatrom (30 mg/kg) | Tylose | 34 (12) | 25 (10) | 9 (12) | 10 (10) | 5 (12) | 11 (10) |
|  | Nafazatrom (100 mg/kg) | Tylose | 25 (16) | 4 (11) | 13 (16) | 10 (11) | 0 (16) | 6 (11) |

It is understood that the specification and examples are illustrative but not limitative of the present invention and that other embodiments within the spirit and scope of the invention will suggest themselves to those skilled in the art.

We claim:

1. A method of inhibiting lipoxygenase in a patient, for the prophylaxis and/or treatment of disorders in cardiac rhythm, which comprises administering to such patient an effective amount of nafazatrom.

* * * * *